United States Patent
Tzirkel-Hancock et al.

(10) Patent No.: US 9,251,704 B2
(45) Date of Patent: Feb. 2, 2016

(54) REDUCING DRIVER DISTRACTION IN SPOKEN DIALOGUE

(71) Applicant: GM Global Technology Operations LLC, Detroit, MI (US)

(72) Inventors: Eli Tzirkel-Hancock, Ra'anana (IL); Omer Tsimhoni, Herzliya (IL)

(73) Assignee: GM GLOBAL TECHNOLOGY OPERATIONS LLC, Detroit, MI (US)

(*) Notice: Subject to any disclaimer, the term of this patent is extended or adjusted under 35 U.S.C. 154(b) by 332 days.

(21) Appl. No.: 13/893,433

(22) Filed: May 14, 2013

(65) Prior Publication Data

US 2013/0321171 A1    Dec. 5, 2013

Related U.S. Application Data

(60) Provisional application No. 61/652,600, filed on May 29, 2012.

(51) Int. Cl.

| | | |
|---|---|---|
| *G05B 19/04* | (2006.01) | |
| *G08G 1/0967* | (2006.01) | |
| *A61B 5/18* | (2006.01) | |

(Continued)

(52) U.S. Cl.
CPC ............... *G08G 1/0967* (2013.01); *A61B 5/18* (2013.01); *G08G 1/09626* (2013.01); *G08G 1/166* (2013.01); *B60W 2540/22* (2013.01); *B60Y 2302/09* (2013.01)

(58) Field of Classification Search
CPC .. G10L 15/24; G08G 1/0967; G08G 1/09626; G08G 1/166; B60W 2540/22; B60Y 2302/09; A61B 5/18
USPC ........................................ 340/576, 573.7, 439
See application file for complete search history.

(56) References Cited

U.S. PATENT DOCUMENTS

| | | | |
|---|---|---|---|
| 7,652,583 B2 * | 1/2010 | Sanchez et al. ............... | 340/575 |
| 8,022,831 B1 * | 9/2011 | Wood-Eyre .................... | 340/575 |

(Continued)

FOREIGN PATENT DOCUMENTS

WO    WO2005/029465 A1    8/2004

OTHER PUBLICATIONS

B. Thomson and S. Young, "Bayesian update of dialogue state: A POMDP framework for spoken dialogue systems," Computer Speech & Language, 2009.

(Continued)

*Primary Examiner* — Daniel Wu
(74) *Attorney, Agent, or Firm* — Mark S. Cohen; Pearl Cohen; Zedek Latzer Baratz LLP

(57) ABSTRACT

Methods and systems for reducing driver distraction and situation non-awareness related to a dialog of an automated dialog system in a vehicle. For a dialog policy learning session, driver distraction is introduced as an input into a penalty assigner that assesses dialog quality, and dialog acts are extended to include dialogs and dialog act presentation styles which reduce driver workload related to dialogs. The automated dialog system policy is developed during the learning process by optimizing the penalties, so that automated dialog workload is reduced in response to increased workload or anticipated workload on the driver. Methods and systems are presented for responding to both actual workload in regular vehicles as well as anticipated workload in autonomous vehicles.

18 Claims, 5 Drawing Sheets

(51) Int. Cl.
*G08G 1/0962* (2006.01)
*G08G 1/16* (2006.01)

(56) References Cited

U.S. PATENT DOCUMENTS

| | | | |
|---|---|---|---|
| 8,260,482 B1* | 9/2012 | Szybalski et al. | 701/23 |
| 8,902,054 B2* | 12/2014 | Morris | 340/439 |
| 9,007,198 B2* | 4/2015 | Gunaratne | 340/439 |
| 2002/0135618 A1* | 9/2002 | Maes et al. | 345/767 |
| 2005/0192730 A1* | 9/2005 | Churchill et al. | 701/45 |
| 2008/0065293 A1* | 3/2008 | Placke et al. | 701/41 |
| 2013/0131905 A1* | 5/2013 | Green et al. | 701/23 |
| 2013/0325482 A1 | 12/2013 | Tzirkel-Hancock et al. | |
| 2014/0136013 A1* | 5/2014 | Wolverton et al. | 701/1 |
| 2014/0207468 A1* | 7/2014 | Bartnik | 704/275 |
| 2015/0091740 A1* | 4/2015 | Bai et al. | 340/901 |

OTHER PUBLICATIONS

B. Thomson, F. Jurčíček, M. Gašić, F. Mairesse, K. Yu, and S. Young. Parameter learning for POMDP spoken dialogue models. Proceedings of SLT, 2010.

S Young, M Gašić, S Keizer, F Mairesse, J Schatzmann, B Thomson, and K Yu, "The hidden information state model: a practical framework for POMDP-based spoken dialogue management," Computer Speech and Language, vol. 24, No. 2, pp. 150-174, Apr. 2010.

Y Zhang, Y Owechko, J Zhang, "Driver Cognitive Workload Estimation: A data driven Perspective", IEEE Intelligent Transportation Systems, Oct. 3-6, 2004.

Office Action for CN Application No. 201310205477.9 date Apr. 23, 2015.

* cited by examiner

REDUCING DRIVER DISTRACTION IN SPOKEN DIALOGUE

CROSS REFERENCE TO RELATED APPLICATION

This application claims benefit of U.S. Provisional Patent Application Ser. No. 61/652,600, filed May 29, 2012, entitled "Reducing driver distraction in spoken dialogue", the disclosure of which is hereby incorporated by reference and the priority of which is hereby claimed pursuant to 37 CFR 1.78 (a) (4) and (5)(i).

BACKGROUND

A driver of a motor vehicle may become distracted under certain conditions, which are typically characterized by increased mental workload. A related situation occurs in a vehicle capable of autonomous operation, where the nominal driver may lose situation awareness, which may be unsafe under certain anticipated workload conditions requiring driver response. Automated spoken and multimodal dialogue systems are becoming more common in motor vehicles and can be a factor in reducing potential distraction and/or reduced situation awareness of the driver.

It is thus desirable to have methods for reducing driver distraction and/or reducing driver situation unawareness while engaging in spoken dialogue with an automated dialogue system. This goal is met by the present invention.

SUMMARY

Embodiments of the invention provide systems and methods for reducing user distraction associated with automated dialogue by monitoring user workload, by providing extended system dialogue acts to compensate for distraction, and by modifying the reward that assesses dialogue performance in order to optimize automated dialogue responsiveness that decreases user distraction associated with automated dialogue.

In a similar fashion, additional embodiments of the invention provide systems and methods for reducing user situation non-awareness associated with automated dialogue in an autonomous vehicle or similar system. According to embodiments of the invention, the terms "situation non-aware" and "situation non-awareness" connote at least a partial unawareness of the full situation in which the autonomous motor vehicle is operating. The driver may have some awareness of the situation, but is potentially lacking the full awareness that a situation-aware driver would be expected to have. A situation-aware driver has sufficient cognitive capacity directed to the driving task of taking control of the vehicle when necessary. A driver with impaired situation-awareness lacks information to take responsible control of the vehicle should the need arise.

Embodiments of the invention may be applied advantageously in a broad range of situations where a human user participates in automated dialogue while operating, or supervising the operation of, apparatus or systems. In certain circumstances the human user may be faced by a high workload burden and may become distracted from the operation of the apparatus or systems. In cases where the user is supervising or overseeing the operation of apparatus or systems, the user may have a heavy anticipated workload and become non-aware of the present situation and factors thereof that could affect the operation which the user is supervising.

For clarity of illustration, the present disclosure details certain embodiments of the invention which are applicable to the non-limiting example of a user who is a driver of a motor vehicle. The case of users who are supervising or overseeing the operation of apparatus or systems is likewise illustrated herein by the non-limiting example of a user who is nominally a driver of an autonomous motor vehicle. It is understood, however, that embodiments of the present invention are broadly applicable to other and more general cases as well. In another non-limiting example, a user who operates an industrial process system and/or supervises the operation of an industrial process system can also benefit from embodiments of the present invention.

Distraction and Situation Non-Awareness

In order to safely and effectively handle a motor vehicle, the driver must continually receive sensory input from many different sources, and respond appropriately and in a timely fashion to those inputs. There is a component of the accumulated workload which is associated with the driver's participation in automated dialogues, and this factor is addressed in the present disclosure.

If the cognitive workload in managing the inputs and responses exceeds a certain level, the driver may become distracted from the task of driving, with potentially serious consequences. A person who is nominally the "driver" of an autonomous vehicle, however, does not have the same ongoing responsibilities. The term "autonomous vehicle" herein denotes a vehicle which has one or more automated systems for performing one or more common driving tasks without direct driver involvement. Examples of systems for autonomous vehicles include, but are not limited to: autopilot systems for aircraft and ships; and cruise control systems and automated lane-centering systems for automobiles and trucks. Although such systems can alleviate considerable workload from the pilot or driver, they may not necessarily be able to handle all situations which may arise. Thus, a trained human operator, designated as the nominal "pilot" or "driver" supervises or oversees the operation of the autonomous vehicle, and is intended to be able to take over partial or full control in the event that a situation arises which the automated system cannot fully handle. In the non-limiting example of a cruise-control system, the driver may have to intervene by applying the brake, should traffic conditions suddenly change.

The driver of an autonomous vehicle may be relieved of much of the driving workload, but must nevertheless remain alert to the present situation at all times, and must remain ready to intervene as necessary. Thus, in place of the workload itself, the driver of an autonomous vehicle has an anticipated workload. The anticipated workload may be similar in some respects to the actual workload handled by an actual driver, and in some cases may even exceed the workload of actual driving, such as in a case where sudden intervention is required. According to certain embodiments of the invention, if the driver is situation non-aware and the anticipated workload exceeds a certain level, then the potential for serious consequences exists.

Therefore, according to certain embodiments of the invention, an increase in anticipated workload for the driver of an autonomous vehicle can lead to a potentially-dangerous condition if the driver is situation non-aware, paralleling the case where an increase in workload for the driver of a regular vehicle can lead to a condition of driver distraction.

FIG. 1 conceptually illustrates the regimes of interest according to certain embodiments of the present invention. A regime set 100 applies to the driver of a regular vehicle, and a regime set 130 applies to the driver of an autonomous vehicle.

Basic regimes 151 pertain to measurement. In a regime 101 the workload associated with driving is measured for the driver of a regular vehicle, and in a regime 131 the anticipated workload associated with driving an autonomous vehicle is measured. Secondary regimes 153 pertain to control of automated dialogues. In a regime 103 the workload associated with automated dialogue in a regular vehicle can be controlled, and in a regime 133 the workload associated with automated dialogue in an autonomous vehicle can be controlled. Optimization regimes 155 provide latitude for adjusting the control of regimes 153. A regime 105 provides latitude to keep the combined driving workload 101 and automated dialogue workload 103 below a distraction threshold 110. According to an embodiment of the invention, distraction threshold 110 is a conceptual threshold rather than an operational threshold. In this embodiment, the system seeks to reduce distraction based on past experience actualized in a learning phase (as discussed below), in place of measuring the distraction directly.

In a region 107 below threshold 110 the driver is not distracted, whereas in a region 109 above threshold 110 the driver is distracted. Likewise, a regime 135 provides latitude to keep the combined driving anticipated workload 131 and automated dialogue workload 133 below a situation non-awareness threshold 140. In a region 137 below threshold 140 the driver is situation-aware, whereas in a region 139 above threshold 140 the driver is situation non-aware.

Reducing Distraction and Situation Non-Awareness

According to certain embodiments of the invention, an offline learning process is used to develop a new dialogue policy for an automated dialogue system using a training database of example dialogues. The new dialogue policy is developed through a learning process which confers penalties for creating dialogues which empirically create distraction/situation non-awareness. (In these embodiments, the term "penalty" denotes a negative reward.) Then, in dialogue-time situations, the new dialogue policy reduces workload/anticipated workload if the dialogue is similar to dialogue examples seen in the training process exceeding a threshold.

In this fashion, embodiments of the invention can optimize the automated dialogue to reduce the levels of distraction/situation non-awareness.

Therefore, according to an embodiment of the invention there is provided a method for reducing user distraction associated with interaction with an automated dialogue system, the method comprising:
receiving, by a processor, a user workload parameter;
responsively to the user workload parameter, controlling the automated dialogue system to perform a system dialogue turn that reduces the user workload associated with interacting with the automated dialogue system, wherein the system dialogue turn includes a dialogue act selected from a group consisting of:
a workload-reducing dialogue act; and
a regular dialogue act modified by a workload-reducing dialogue modification.

Also, according to another embodiment of the invention, there is provided a method for reducing user situation non-awareness associated with an automated dialogue system, the method comprising:
receiving, by a processor, a user anticipated workload parameter;
responsively to the user anticipated workload parameter, controlling the automated dialogue system to perform a system dialogue turn that reduces the user workload associated with interacting with the automated dialogue system, wherein the system dialogue turn includes a dialogue act selected from a group consisting of:
a workload-reducing dialogue act; and
a regular dialogue act modified by a workload-reducing modification.

In addition, according to a further embodiment of the invention, there is provided a dialogue system for reducing user distraction associated with interaction with automated dialogue, the system comprising:
a dialogue control unit;
a storage device containing a dialogue policy;
a workload estimation unit operative to:
receive a workload parameter indicative of a user workload; and
compute a workload estimate; and
input the workload estimate into the dialogue control unit.

Moreover, according to still another embodiment of the invention, there is provided a dialogue system for reducing user situation non-awareness associated with interaction with automated dialogue, the system comprising:
a dialogue control unit;
a storage device containing a dialogue policy;
an anticipated workload estimation unit operative to:
receive an anticipated workload parameter indicative of an anticipated user workload; and
compute an anticipated workload estimate; and
input the anticipated workload estimate into the dialogue control unit.

BRIEF DESCRIPTION OF THE DRAWINGS

The subject matter disclosed may best be understood by reference to the following detailed description when read with the accompanying drawings in which.

Figure 1:
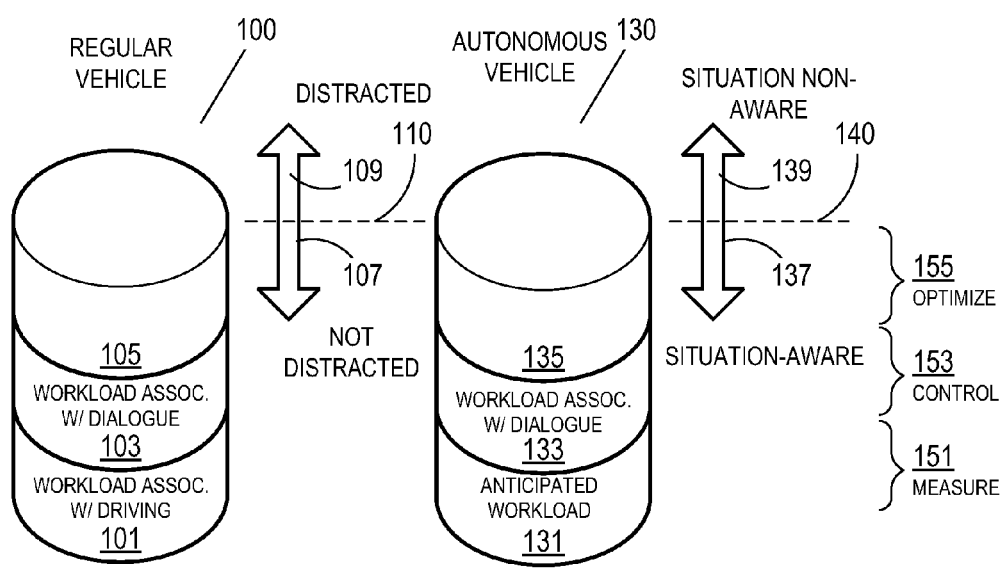
FIG. 1 illustrates operational regimes for reducing driver distraction and situation non-awareness, according to certain embodiments of the invention.

For simplicity and clarity of illustration, reference numerals may be repeated among the figures to indicate corresponding or analogous elements.

DETAILED DESCRIPTION

Figure 2A:
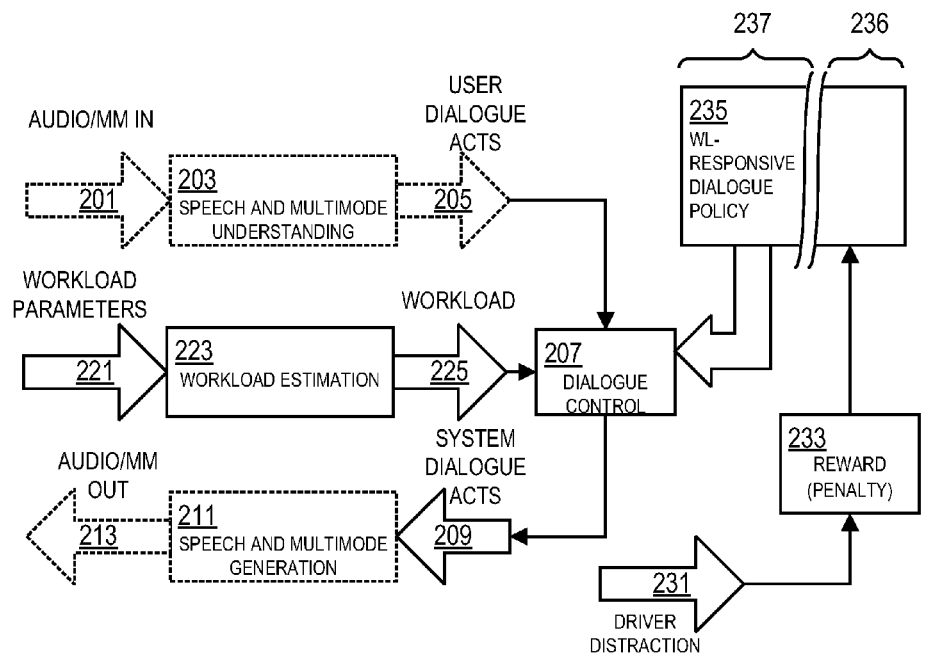
FIG. 2A conceptually illustrates a system according to certain embodiments of the invention, for reducing user distraction in real time.

FIG. 2A conceptually illustrates a system according to certain embodiments of the invention, for reducing distraction in real time for a driver of a regular motor vehicle. An input stage 201 receives speech audio and/or multimodal input to a speech and multimodal understanding unit 203, which outputs processed user dialogue acts 205 into a dialogue control unit 207. In response, dialogue control unit 207 outputs system dialogue acts 209 into a speech and multimodal generation unit 211 for generating speech audio and/or multimodal output 213. In these embodiments, one or more workload parameters 221 are input into a workload estimation unit 223 which outputs a workload measure 225 into dialogue control unit 207. A workload-responsive dialogue policy 235 is available to dialogue control unit 207 for responding to high workload situations with appropriate workload-reducing system dialogue acts 209. Workload estimates may be prepared according to factors including, but not limited to: vehicle parameters, such as steering, brakes, and safety systems; road conditions, such as road bends and traffic; weather conditions, such as rain and fog; time of day; and driver attributes, such as eye, head, and hand movements.

According to certain embodiments of the invention, a workload estimation may be obtained from factors including, but not limited to:
    vehicle parameters, such as:
        steering,
        brakes,
        safety systems
    road conditions, such as
        road-bends or
        traffic
    weather conditions, such as
        heavy-rain or
        fog
    time of day
    driver attributes, such as movement of
        eyes
        head, and
        hands In another embodiment of the invention, workload can be estimated according to a user model. These different embodiments regarding workload estimation can be combined together or used separately.

Further embodiments of the invention provide an estimate of future workload, which may be useful for adjusting dialogue policy to reduce future driver distraction. In these embodiments, workload may be predicted according to factors including, but not limited to:
    road conditions
    weather conditions, and
    time of day According to these embodiments, to prepare workload-responsive dialogue policy 235, a driver distraction input 231 is used as penalties 233 in a learning process, as described below. The output of the learning process is used to create dialogue policy 235. Dialogue policy 235 thus bridges between the learning process—shown in FIG. 2A conceptually as an off-line creation phase 236 of dialogue policy 235—and the interactive dialogue system—shown in FIG. 2A conceptually as a dialogue-time application 237 of dialogue policy 235.

Figure 2B:
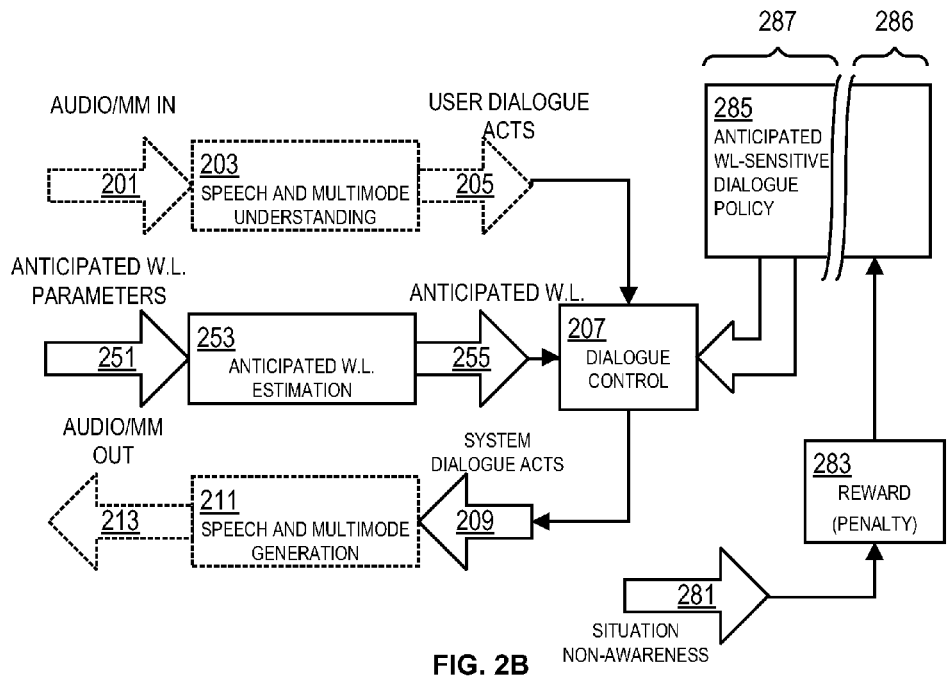
FIG. 2B conceptually illustrates a system according to certain embodiments of the invention, for reducing user situation non-awareness in real time.

FIG. 2B conceptually illustrates a system according to certain embodiments of the invention, for reducing situation non-awareness in dialogue time for a driver of an autonomous motor vehicle. As before, an input stage 201 receives speech audio and/or input to a speech and multimodal understanding unit 203, which outputs processed user dialogue acts 205 into a dialogue control unit 207. In response, dialogue control unit 207 outputs system dialogue acts 209 into a speech and multimodal generation unit 211 for generating speech audio and/or multimodal output 213. In these embodiments, one or more anticipated workload parameters 251 are input into an anticipated workload estimation unit 253 which outputs an anticipated workload measure 255 into dialogue control unit 207. An anticipated workload-responsive dialogue policy 285 is available to dialogue control unit 207 for responding to high anticipated workload situations with appropriate workload-reducing system dialogue acts 209.

Anticipated workload is the cognitive workload the driver would incur should it become necessary to take over control of the vehicle. If the driver is participating in an automated dialogue, this may impact situation awareness, particularly in an environment of high anticipated workload. According to certain embodiments of the invention, an anticipated workload estimate may be obtained from factors including, but not limited to:
    vehicle parameters, such as:
        steering,
        brakes,
        safety systems
    road conditions, such as
        road-bends or
        traffic
    weather conditions, such as
        heavy-rain or
        fog
    time of day According to these embodiments, a prediction of anticipated workload may be useful for adjusting the dialogue policy to increase future situation awareness, and anticipated workload may be predicted according to factors including, but not limited to:
    road conditions
    weather conditions, and
    time of day According to these embodiments, to prepare anticipated workload-responsive dialogue policy 285, a driver situation non-awareness input 281 is used as penalties 283 in a learning process, as described below. The output of the learning process is used to create dialogue policy 285. Dialogue policy 285 thus bridges between the learning process—shown in FIG. 2B conceptually as an off-line creation phase 286 of dialogue policy 285—and the interactive dialogue system—shown in FIG. 2B conceptually as a dialogue-time application 287 of dialogue policy 285.

Figure 3A:
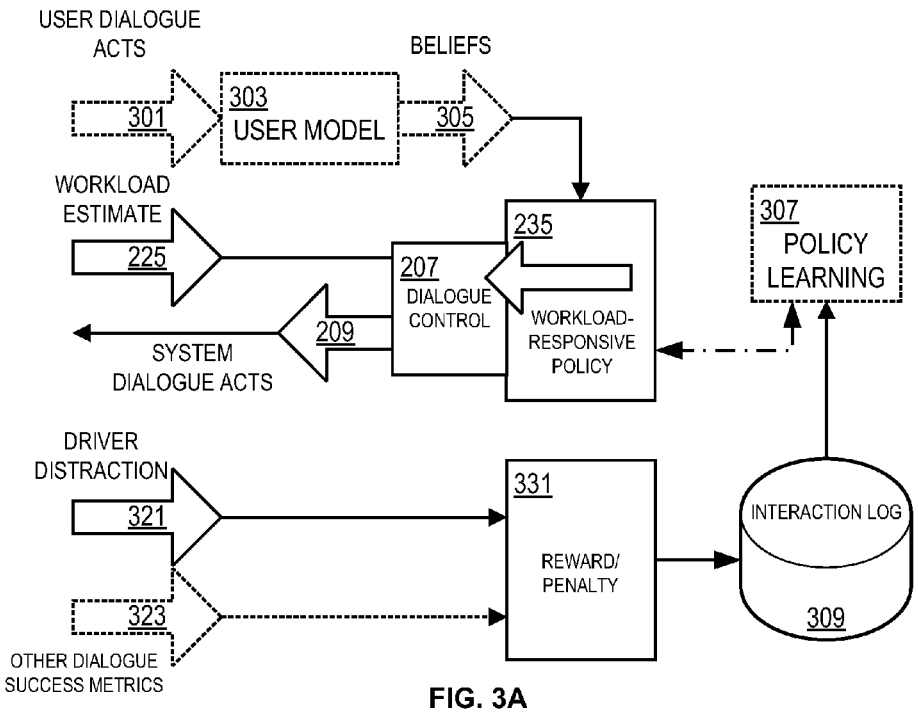
FIG. 3A conceptually illustrates a system according to certain embodiments of the invention, for offline policy learning to reduce user distraction.

FIG. 3A conceptually illustrates a system according to certain embodiments of the invention, for offline policy learning to reduce driver distraction. User dialogue acts 301 are input into a user model 303, the output of which are a set of beliefs 305 that are used as input to workload-responsive dialogue policy 235, which has been formulated through an off-line policy learning process 307. The new policy developed through this process is therefore sensitive to the beliefs. As also illustrated in FIG. 2A, policy 235 is used to govern dialogue control unit 207 to output system dialogue acts 209 in response to the beliefs and workload estimate 225.

Policy learning process 307 receives input from an interaction log 309 with reward/penalty 331 input to guide the learning process in creating a policy that meets the desired goal of reducing driver distraction. Input to reward/penalty 331 includes penalties according to a driver distraction assessment 321. Driver distraction assessment 321 can be obtained from a driver's subjective impression of being distracted. Because the learning process takes place off-line, driver assessments can be obtained after completion of the driving session, in a vehicle or a vehicle simulator, in which the dialogues recorded in interaction log 309 were obtained.

According to various embodiments of the invention, an off-line process for policy learning takes place in a laboratory, for which a reward is also assigned off-line. In other embodiments, policy learning takes place in the vehicle itself, or an off-vehicle server, such as at a scheduled time, or after sufficient dialogue is recorded in the dialogue log, in cases where the reward is measured automatically.

Besides direct feedback from the driver, visual inspection of driver interaction and/or performance-metrics can be used, such as braking response time given the measured headway from a lead vehicle and observation of driver head and eye movement. Driver feedback is typically limited to off-line availability, but automated assessments may be done in real-time during driving sessions. In addition to driver distraction assessment 321, which involves penalties for distraction, other dialogue metrics 323 can be used, some of which may involve rewards.

Figure 3B:
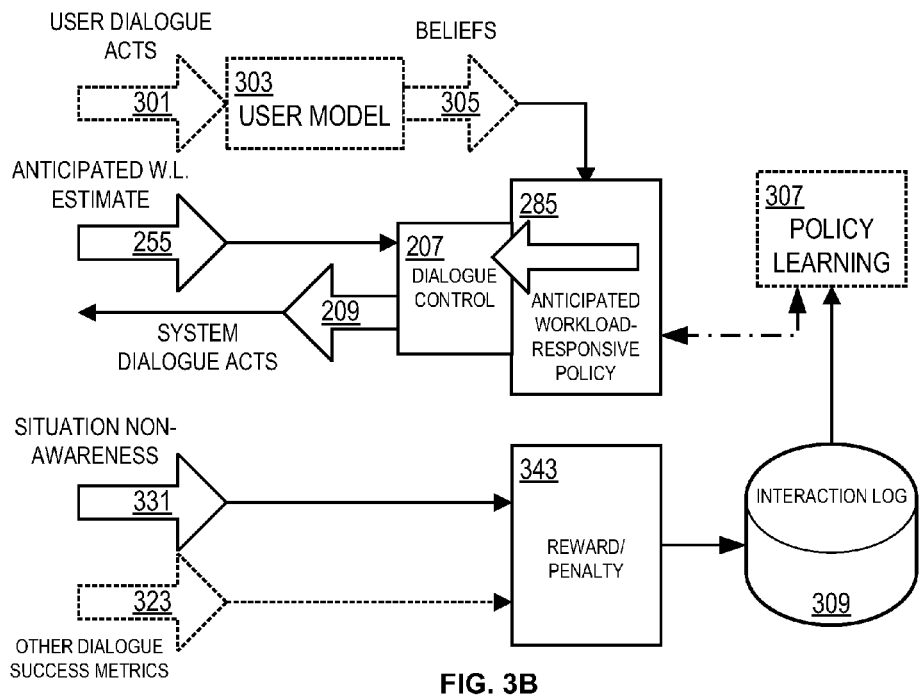
FIG. 3B conceptually illustrates a system according to certain embodiments of the invention, for offline policy learning to reduce user situation non-awareness.

In a similar manner, FIG. 3B conceptually illustrates a system according to certain embodiments of the invention, for offline policy learning to reduce driver situation non-awareness in an autonomous vehicle. User dialogue acts 301 are input into a user model 303, the output of which are a set of beliefs 305 that are used as input to anticipated workload-responsive dialogue policy 285, which has been formulated through off-line policy learning process 307. As also illustrated in FIG. 2B, policy 285 is used to govern dialogue control unit 207 to output system dialogue acts 209 in response to anticipated workload estimate 255. Also in a similar manner, reward/penalty 343 receives input from a driver situation non-awareness assessment 331.

According to certain embodiments of the invention, dialogue-time measurement of driver situation awareness enables policy learning, and driver situation awareness may be obtained in ways including, but not limited to:
- as feedback from the driver;
- by visual inspection of driver interactions; and
- by measuring driver eye and head movement, e.g.
  - driver's eyes focused on the road implies a high driver situation awareness; but
  - driver's eyes focused elsewhere than on the road implies a low driver situation awareness.

Driving Modes in an Autonomous Vehicle

There are two modes for operating an autonomous vehicle: an autonomous mode, where one or more autonomous systems are in control of respective vehicle operating functions; and a driver control mode, where the driver assumes control of the vehicle. Autonomous control can be partial control of vehicle operating functions, a non-limiting example of which is automatic cruise control in a vehicle. According to certain embodiments of the invention, an automated dialogue system in an autonomous vehicle should be able to handle switching between these two modes. According to an embodiment of the invention, this is done by switching between two appropriate dialogue policies; in this embodiment, the learning phase policy parameters are developed separately, and at dialogue time the appropriate policy is selected, consistent with the driving mode. In another embodiment of the invention, there is a combined dialogue policy that supports both modes, and at dialogue time the mode is input to the policy along with both workload and anticipated workload estimates, and with penalty for driver distraction and penalty for driver situation non-awareness.

Method

Figure 4A:
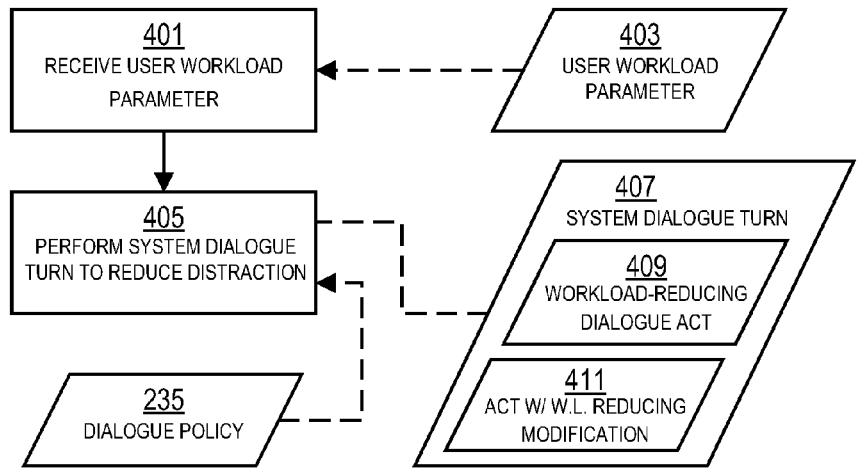
FIG. 4A is a flowchart of a method according to certain embodiments of the invention, for reducing user distraction in real time.

FIG. 4A is a flowchart of a method according to certain embodiments of the invention, for reducing driver distraction during a dialogue.

In a step 401 a driver workload parameter 403 is received. Then, in a step 405 a system dialogue turn 407 is performed according to workload-responsive dialogue policy 235. According to these embodiments, system dialogue turn 407 includes a workload-reducing dialogue act 409 and/or a regular system dialogue turn with a workload-reducing modification 411.

Figure 4B:
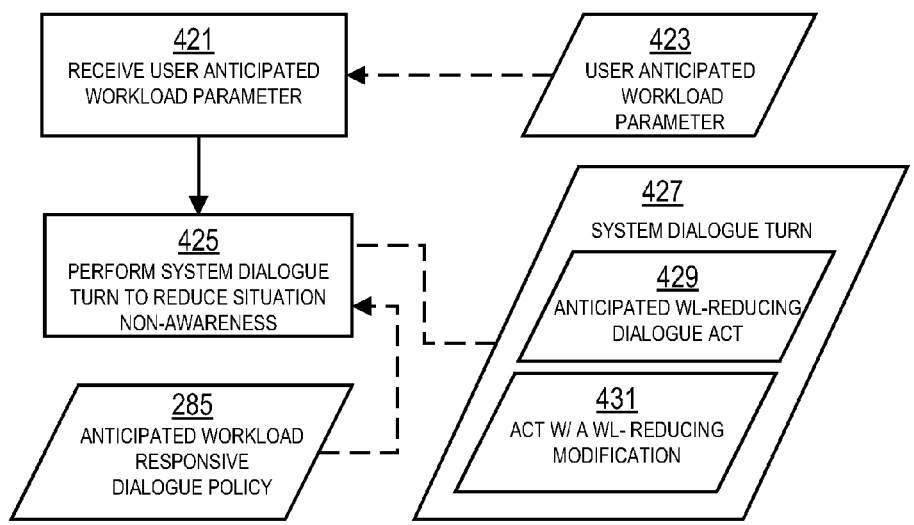
FIG. 4B is a flowchart of a method according to certain embodiments of the invention, for reducing user situation non-awareness in real time.

In a similar manner, FIG. 4B is a flowchart of a method according to other embodiments of the invention, for reducing driver situation non-awareness in an autonomous vehicle during a dialogue.

In a step 421 a driver anticipated workload parameter 423 is received. Then, in a step 425 a system dialogue turn 427 is performed according to anticipated workload-responsive dialogue policy 285. According to these embodiments, system dialogue turn 427 includes an anticipated workload-reducing dialogue act 429 and/or a regular system dialogue turn with an anticipated workload-reducing modification 431.

According to the above embodiments, workload-reducing and anticipated workload-reducing dialogue turns may have features including, but not limited to: pauses and suggestions for pauses (see below); termination of dialogue and suggestions for terminating dialogue. Workload-reducing and anticipated workload-reducing modifications may have features including, but not limited to: breaking up dialogue turns into simpler sentences; presenting alternatives sequentially, rather than together; and phrasing questions for answering by "yes-no" responses; preferring speech modality to tactile and visual modality (see below).

Certain embodiments of the invention provide a spectrum of pause handling, and termination ranging as follows by degree of user involvement, which is selectable by the system:
- Pause with or without a prompt, until workload is reduced;
- Prompt the user before pausing and allow the user a limited time to cancel the pause;
- Suggest pausing as a choice to the user;
- Pause according to user request;
- Pause until instructed otherwise; and
- Terminate the dialogue
- Prompt the user before terminating and allow the user a limited time to cancel;
- Suggest terminating the dialogue to the user
- Terminate upon user request.

According to related embodiments of the present invention, the difference between pausing a dialogue and terminating the dialogue is that a paused dialogue may be resumed at a later time from the point at which the dialogue was paused, whereas a terminated dialogue is stopped and may not be resumed (but may be restarted). The terms "suspend", "suspending", "suspension", etc., herein denote that a dialogue has been interrupted by either being paused or being terminated. Whether or not a suspended dialogue may be later resumed depends on whether the dialogue was paused or terminated, but in either case the dialogue is interrupted at the time the suspension goes into effect.

Figure 5:
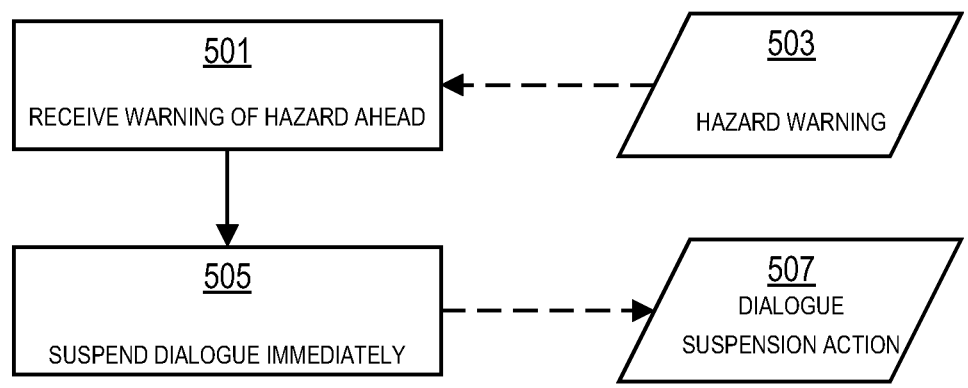
FIG. 5 is a flowchart of a method according to specific embodiments of the invention, for reducing driver distraction in real time.

FIG. 5 is a flowchart of a method according to specific embodiments of the invention. In a step 501 a hazard warning 503 is received. Hazard warning 503 can be signaled by a variety of presently-known methods, including, but not limited to: detection of a hazard ahead by an on-board radar system; and hazard notification by a navigational system, based on road condition information supplied to the navigational system. In a related embodiment, the hazard warning includes a warning of a braking condition of another vehicle ahead of the vehicle. In a step 505, in response to hazard warning 503, the dialogue is immediately suspended via an immediate dialogue suspension action 507.

The method illustrated in FIG. 5 may also be considered as a special case of the method illustrated in FIG. 4A, wherein user workload parameter 403 includes hazard warning 503 that a hazard has been detected, and system dialogue turn 407 includes immediate dialogue suspension action 507. In this case, immediate dialogue suspension action 507 is included in workload-reducing dialogue act 409 or in workload-reducing dialogue modification 411. In a related embodiment, workload estimation 223 (FIG. 2A) includes hazard warning 503. In another related embodiment, workload estimation 223 includes immediate dialogue suspension action 507.

The method illustrated in FIG. 5 may additionally be considered as a special case of the method illustrated in FIG. 4B, wherein user anticipated workload parameter 423 includes hazard warning 503 that a hazard has been detected, and system dialogue turn 427 includes immediate dialogue suspension action 507. In this case, immediate dialogue suspension action 507 is included in anticipated workload-reducing dialogue act 429 or in anticipated workload-reducing dialogue modification 431. In a related embodiment, anticipated workload estimation 253 (FIG. 2B) includes hazard warning 503. In another related embodiment, anticipated workload estimation 253 includes immediate dialogue suspension action 507.

According to embodiments of the invention, a dialogue may be simplified by one or more of the following:

Breaking up compound requests for information to requests for separate single items of information;
Presenting alternatives separately in sequential sentences rather than together in a single sentence; and
Presenting questions in low-level or yes/no answer form.

According to other embodiments of the invention, a prediction of upcoming increased workload can trigger the speeding up of a dialogue. For example, if the driver is approaching an area of congested traffic or other abnormal driving conditions, the automated dialogue system can receive a prediction that workload will soon increase, and may decide to accelerate an ongoing dialogue so that the dialogue will complete before the workload increases. A dialogue may be speeded up by one or more of the following:

Reducing the number of prompts by aggregating information in fewer prompts;
Presenting information visually, rather than aurally; and
Using implicit confirmation rather than explicit confirmation. For example, if the driver requested information on nearby Chinese restaurants, the dialogue system could respond with an implicit confirmation such as "What price range Chinese restaurant do you seek?" rather than first asking for explicit confirmation that the request was for Chinese restaurants.

Computer Product

A computer product according to the above method embodiments includes a set of executable commands for performing the one or both of the above methods on a computer, wherein the executable commands are contained within a tangible computer-readable non-transitory data storage medium including, but not limited to: computer media such as magnetic media and optical media; computer memory; semiconductor memory storage; flash memory storage; data storage devices and hardware components; and the tangible non-transitory storage devices of a remote computer or communications network; such that when the executable commands of the computer product are executed, the computer product causes the computer to perform one or both of the above methods.

In these embodiment, a "computer" is any data processing apparatus for executing a set of executable commands to perform a method of the present invention, including, but not limited to: personal computer; workstation; server; gateway; router; multiplexer, demultiplexer; modulator, demodulator; switch; network; processor; controller; digital appliance, tablet computer; mobile device, mobile telephone; any other device capable of executing the commands While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for reducing user distraction associated with interaction with an automated dialogue system, the method comprising:
   receiving, by a processor, a user workload parameter;
   responsively to the user workload parameter, controlling the automated dialogue system to perform a system dialogue turn that reduces the user workload associated with interacting with the automated dialogue system, wherein the system dialogue turn includes a dialogue act selected from a group consisting of:
      a workload-reducing dialogue act; and
      a regular dialogue act modified by a workload-reducing dialogue modification;
   detecting a user distraction level for a plurality of dialogues;
   responsive to detecting the user distraction level, computing a penalty value for assessing a dialogue quality according to at least the user distraction level for a dialogue of the plurality of dialogues;
   storing the penalty value in a database which includes the plurality of dialogues; and
   computing a dialogue policy for a controller of the automated dialogue system according to the database.

2. The method of claim 1, wherein the workload-reducing dialogue act comprises an act selected from a group consisting of:
   a dialogue pause;
   a suggestion of a dialogue pause;
   a dialogue termination;
   a suggestion of a dialogue termination.

3. The method of claim 2, further comprising a spectrum of pause-handling and termination handling choices ranging by degree of user involvement.

4. The method of claim 1, wherein the workload-reducing dialogue modification comprises a dialogue modification selected from a group consisting of:
   a switch to voice modality;
   breaking up compound prompts into items;
   a change to a yes/no prompt; and
   speeding up of a dialogue.

5. The method of claim 4, wherein the speeding up of a dialogue act is in response to a predicted workload increase.

6. The method of claim 1, wherein the user workload parameter includes a hazard warning of a hazard ahead of the vehicle, and wherein at least one of the workload reducing act or the workload reducing dialogue modification includes an immediate suspension of the dialogue.

7. The method of claim 6, wherein the hazard warning includes a warning of a braking condition of another vehicle ahead of the vehicle.

8. A method for reducing user situation non-awareness associated with an automated dialogue system, the method comprising:

receiving, by a processor, a user anticipated workload parameter;

responsively to the user anticipated workload parameter, controlling the automated dialogue system to perform a system dialogue turn that reduces the user workload associated with interacting with the automated dialogue system, wherein the system dialogue turn includes a dialogue act selected from a group consisting of:

a workload-reducing dialogue act; and a regular dialogue act modified by a workload-reducing modification;

detecting a user situation non-awareness level for a plurality of dialogues stored in a database;

responsive to detecting the user situation non-awareness level, computing a penalty value for assessing a dialogue quality according to at least the user situation non-awareness; and computing a dialogue policy for a controller of the automated dialogue system according to the database.

9. The method of claim 8, wherein the workload-reducing dialogue act comprises an act selected from a group consisting of:

a dialogue pause;

a suggestion of a dialogue pause;

a dialogue termination;

a suggestion of a dialogue termination.

10. The method of claim 9, further comprising a spectrum of pause-handling and termination handling choices ranging by degree of user involvement.

11. The method of claim 6, wherein the workload-reducing dialogue modification comprises a dialogue modification selected from a group consisting of:

a switch to voice modality;

breaking up compound prompts into items;

a change to a yes/no prompt; and speeding up of a dialogue.

12. The method of claim 11, wherein the speeding up of a dialogue act is in response to a predicted anticipated workload increase.

13. A dialogue system for reducing user distraction associated with interaction with automated dialogue, the system comprising:

a dialogue control unit;

a storage device containing a dialogue policy;

a workload estimation unit operative to:

receive a workload parameter indicative of a user workload;

compute a workload estimate;

input the workload estimate into the dialogue control unit;

perform a system dialogue turn that reduces the user workload associated with interacting with the automated dialogue system, wherein the system dialogue turn includes a dialogue act selected from a group consisting of:

a workload-reducing dialogue act; and a regular dialogue act modified by a workload-reducing dialogue modification;

detect a user distraction level for a plurality of dialogues;

responsive to detecting the user distraction level, compute a penalty value for assessing a dialogue quality according to at least the user distraction level for a dialogue of the plurality of dialogues;

store the penalty value in a database which includes the plurality of dialogues; and compute a dialogue policy for a controller of the automated dialogue system according to the database.

14. The dialogue system of claim 13, wherein the workload parameter includes a hazard warning of a hazard ahead of the vehicle, and wherein the workload estimate includes the hazard warning.

15. The dialogue system of claim 14, wherein the hazard warning includes a warning of a braking condition of another vehicle ahead of the vehicle.

16. A dialogue system for reducing user situation non-awareness associated with interaction with automated dialogue, the system comprising:

a dialogue control unit;

a storage device containing a dialogue policy;

an anticipated workload estimation unit operative to:

receive an anticipated workload parameter indicative of an anticipated user workload;

compute an anticipated workload estimate;

input the anticipated workload estimate into the dialogue control unit;

perform a system dialogue turn that reduces the user workload associated with interacting with the automated dialogue system, wherein the system dialogue turn includes a dialogue act selected from a group consisting of:

a workload-reducing dialogue act; and a regular dialogue act modified by a workload-reducing modification; detect the user situation non-awareness level for a plurality of dialogues stored in a database;

responsive to detecting the user situation non-awareness level, compute a penalty value for assessing a dialogue quality according to at least the user situation non-awareness; and compute a dialogue policy for the dialogue control unit according to the database.

17. The dialogue system of claim 16, wherein the anticipated workload parameter includes a hazard warning of a hazard ahead of the vehicle, and wherein the anticipated workload estimate includes the hazard warning.

18. The dialogue system of claim 17, wherein the hazard warning includes a warning of a braking condition of another vehicle ahead of the vehicle.

* * * * *